(12) United States Patent
Thorner

(10) Patent No.: US 7,442,706 B2
(45) Date of Patent: Oct. 28, 2008

(54) METHODS FOR TREATING SARCOPENIA WITH A GROWTH HORMONE SECRETAGOGUE

(76) Inventor: Michael O. Thorner, 906 Fendall Ter., Charlottesville, VA (US) 22903

( * ) Notice: Subject to any disclaimer, the term of this patent is extended or adjusted under 35 U.S.C. 154(b) by 0 days.

(21) Appl. No.: 11/685,245

(22) Filed: Mar. 13, 2007

(65) Prior Publication Data

US 2007/0219226 A1    Sep. 20, 2007

Related U.S. Application Data

(60) Provisional application No. 60/782,348, filed on Mar. 15, 2006.

(51) Int. Cl.
*A61K 31/44* (2006.01)

(52) U.S. Cl. .................................... 514/278

(58) Field of Classification Search ............... None
See application file for complete search history.

(56) References Cited

U.S. PATENT DOCUMENTS

| 6,194,402 B1 | 2/2001 | Bach et al. | |
| 6,380,184 B1 * | 4/2002 | Li | 514/213.01 |
| 2002/0028838 A1 | 3/2002 | MacLean et al. | |

OTHER PUBLICATIONS

Bach, Mark A., et al.; The Effects of MK-0677, an Oral Growth Hormone Secretagogue, in Patients With Hip Fractures. J. Am. Geriatr. Soc. 2004, 52(4), 516-523.

Chapman, Ian M., et al.; Stimulation of the Growth Hormone (GH)-Insulin-Like Growth Factor-I Axis by Daily Oral Administration of a GH Secretogogue (MK-677) in Healthy Elderly Subjects. J. Clin. Endocrinol. Metab. 1996, 81(12), 4249-4257.

Chapman, Ian M., et al.; Oral Administration of Growth Hormone (GH) Releasing Peptide-Mimetic MK-677 Stimulates the GH/Insulin-Like Growth Factor-I Axis in Selected GH-Deficient Adults. J. Clin. Endocrinol. Metab. 1997, 82(10), 2455-3463.

Doherty, Timothy J.; Physiology of Aging Invited Review: Aging and Sarcopenia. J. Appl. Physiol. 2003, 95, 1717-1727.

Goodpaster, Bert H., et al.: The Loss of Skeletal Muscle Strength, Mass, and Quality in Older Adults: The Health, Aging and Body Composition Study. J. Gerontol. Med. Sci. 2006, 61A(10), 1059-1064.

Murphy, M. G., et al.; Effect of Alendronate and MK-677 (a Growth Hormone Secretagogue), Individually and in Combination, on Markers of Bone Turnover and Bone Mineral Density in Postmenopausal Osteoporotic Women. J. Clin. Endocrinol. Metab. 2001, 83(3), 1116-1125.

Wolfe, Robert R.; The Underappreciated Role of Muscle in Health and Disease. An. J. Clin. Nutr. 2006, 84, 475-482.

Smith, Roy G.: Development of Growth Hormone Secretagogues; Endocrine Reviews (26) pp. 346-360, date not available.

(Continued)

*Primary Examiner*—Raymond J Henley, III

(74) *Attorney, Agent, or Firm*—Feldman Gale P.A.

(57) ABSTRACT

The present invention relates to methods for treating sarcopenia with a growth hormone secretagogue.

14 Claims, 5 Drawing Sheets

OTHER PUBLICATIONS

Murphy, M. G. et al.: Effect of Alendronate and MK-677 (a Growth Hormone Secretagogue), Individually and in Combination, on Markers of Bone Turnover and Bone Mineral Density in Postmenopausal Osteoporotic Women; The Journal of Clinical Endocrinology & Metabolism; vol. 86 No. 3 pp. 1116-1125, date not available.

Svensson, J. et al.: Two-Month Treatment of Obese Subjects with the Oral Growth Hormone (GH) Secretagogue MK-677 Increases GH Secretion, Fat-Free Mass, and Energy Expenditure; Journal of Clinical Endocrinology and Metabolism; vol. 83 No. 2; pp. 362-369, date not available.

Bach, Mark A. et al.: The Effects of MK-0677, an Oral Growth Hormone Secretagogue, in Patients with Hip Fracture; The American Geriatrics Society; JAGS 52: pp. 516-523, 2004.

Hensley, Scott: Death of Pfizer's "Youth Pill" Illustrates Drug Makers' Woes; The Wall Street Journal; http://online.wsj.com/article_email/article_print/SB102028770668599840-1MyQjAxMDA4; pp1-6;WSJ.com, date not available.

* cited by examiner

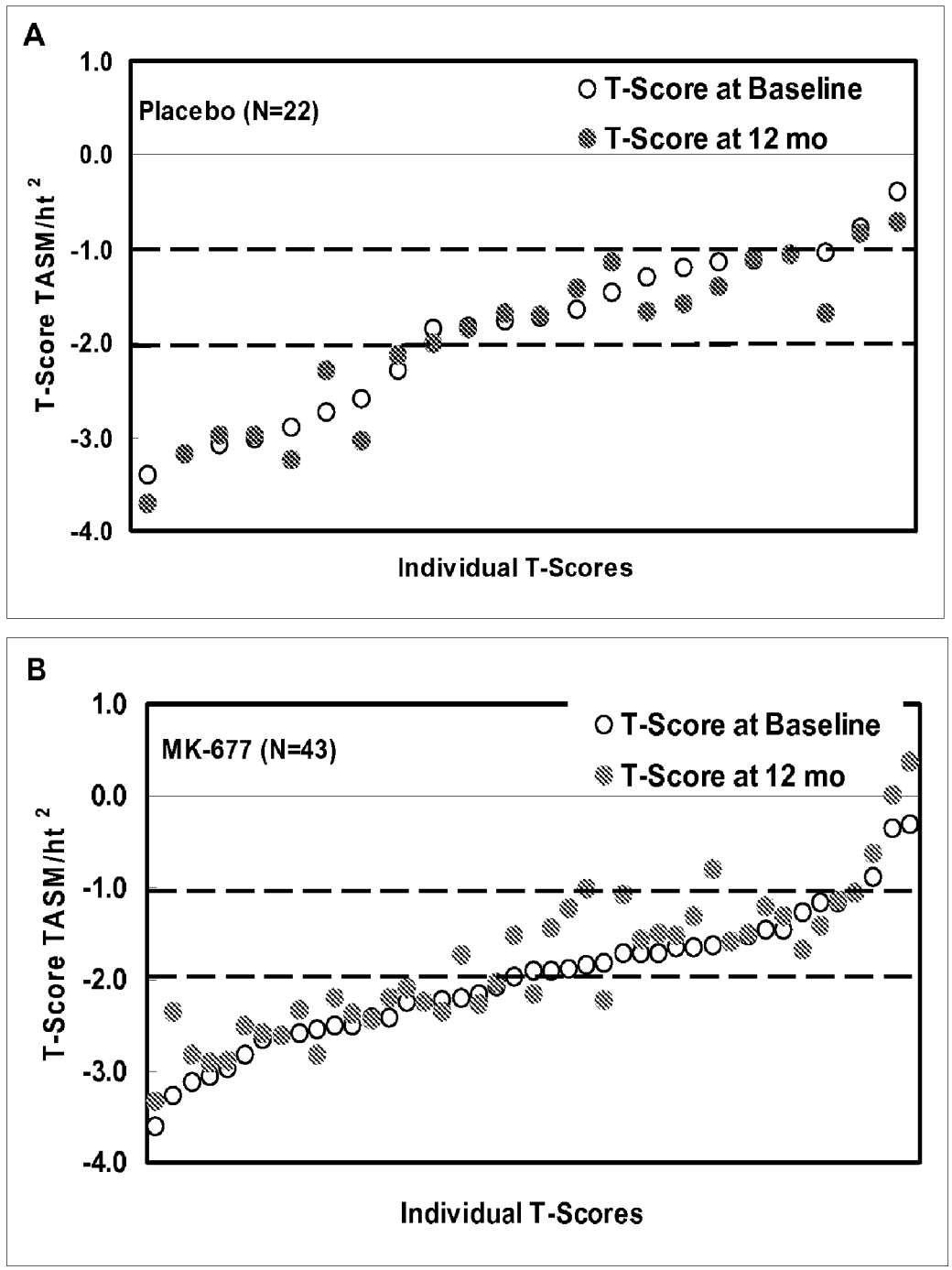
Figures 5A-B

METHODS FOR TREATING SARCOPENIA WITH A GROWTH HORMONE SECRETAGOGUE

US GOVERNMENT RIGHTS

This invention was made with United States Government support under Grant Nos. DK32632 and RR-00847 awarded by the National Institutes of Health. The United States Government may have certain rights in the invention.

FIELD OF THE INVENTION

The present invention relates to methods for treating sarcopenia with a growth hormone secretagogue.

BACKGROUND

Sarcopenia is the reduction in muscle mass that occurs with aging. It is a progressive process that occurs throughout adult life such that by the time a person reaches 80 years of age his or her muscle mass may have declined by as much as 50% from their prime of life in the late teens to early twenties. This reduction of muscle mass is a significant factor in the development of frailty, which is accompanied by falls that lead to fractures and ultimately to morbidity and mortality. Sarcopenia is believed to be associated with metabolic, physiologic, and functional impairments and disability. There are no simple treatments available to prevent it.

Baumgartner et al. (Am J Epidemiol 1998; 147:755-63; 149: 1161) have defined sarcopenia as appendicular skeletal muscle mass (kg/height$^2$ (m$^2$)) being less than two standard deviations below the mean of a young reference group. This is referred to as a "t-score" hereinafter. Baumgartner et al used the data from the New Mexico Elder Health Survey, 1993-1995 to develop a method for estimating the prevalence of sarcopenia and found that the prevalence "increased from 13-24% in persons under 70 years of age to >50% in persons over 80 years of age[.]" The study by Baumgartner et al was one of the first to estimate the extent of the prevalence of sarcopenia.

The physiological mechanism for the decline in muscle mass is unknown. Growth hormone secretion declines progressively from mid puberty, and growth hormone is known to increase muscle mass. Patients with growth hormone deficiency have reduced muscle mass and increased fat mass. Growth hormone replacement increases the muscle mass and leads to a reduction in fat mass.

Growth hormone secretagogues have been developed to enhance growth hormone secretion. A growth hormone secretagogue is a compound that, when administered to a patient, increases the production and/or secretion of growth hormone when compared with baseline plasma concentrations of growth hormone in a normal healthy individual. They act through a growth hormone secretagogue receptor. A natural ligand for this receptor was discovered in 1999, and it is produced in the mucosa of the stomach. It is called ghrelin and has a unique modification at serine in position 3. The modification is that it is N-octonylated.

Ibutamoren mesylate (MK-677) was developed at Merck Research Laboratories as a specific orally active growth hormone secretagogue. Journal of Orthopaedic Research 15:519:527 (1997) states that a growth hormone secretagogue, MK-677, elevated levels of serum insulin-like growth factor-1, which in turn increased the size and strength of the quadriceps muscle in canines during remobilization. J. Clin. Endocrinol. Metab. 83: 320-325, 1998, states that MK-677, an orally active growth hormone secretagogue, reverses diet-induced catabolism.

U.S. Pat. No. 6,194,402 (Bach et al) describes the use of growth hormone secretagogues, including MK-677, for "enhancing the return of a patient to independent living status following acute deconditioning of [a] patient who was living independently prior to such acute deconditioning[.]" (See claim 1.) Bach et al define the term 'acute deconditioning' to indicate the presence of a diminished state in a patient characterized by muscle atrophy and muscle loss which results from specific insult such as immobilization or inactivity brought on by acute illness or injury. In contrast, chronic deconditioning is defined as long-term muscle loss or wasting, i.e., sarcopenia.

Bach et al clearly distinguish between acute deconditioning and sarcopenia. This is because the maintenance of muscle mass depends on two different processes: maintaining function and exercise that allow muscle mass to be maintained or built; and, an ability to maintain muscle mass that depends on nutrition, neural input, and hormonal state. The peak muscle mass is observed at the time of mid-puberty and muscle mass progressively declines and is detectably reduced by the age of 45 years and continues to progressively decline. This decline in muscle mass appears to be dependent on growth hormone secretion, which declines with age. Even Olympic athletes lose muscle mass and function as they age despite regular exercise.

US Patent Publication No. 2002/0028838 (MacLean et al) recites a "[m]ethod for treating age related decline in physical performance in an at-risk patient which comprises administering to the patient a performance enhancing effective amount of a growth hormone secretagogue." (See claim 1.) MacLean et al state that "[t]he term 'at-risk patient' is a patient who exhibits objective evidence of decline in physical performance as measured by established methods of physical performance assessment. Measures of physical performance are objective tests of subjects' performance of standardized tasks, evaluated according to predetermined criteria that may include counting repetitions or timed activity. A decline in physical performance results in increased odds of the patient suffering an adverse event such as an injurious fall and/or fracture. A decline in physical performance may also result in the patient having to be admitted to a nursing home and/or developing functional dependence in activities of daily living." (See paragraph 0173.) This population and this condition are distinct and separate from the population suffering from and the indication of sarcopenia because sarcopenia occurs prior to the development of decline in physical performance. The treatment of sarcopenia is not considered by MacLean et al as this indication occurs long before a patient would be considered "at-risk" by MacLean et al.

In view of the substantially increasing age of the population in developed nations and the inevitability of sarcopenia, it is highly desirable to find a method for treating sarcopenia.

SUMMARY OF THE INVENTION

Accordingly, the present invention provides novel a method for maintaining or increasing muscle mass to treat sarcopenia.

The present invention also relates to compositions useful for maintaining or increasing muscle mass to treat sarcopenia.

These and other aspects, which will become apparent during the following detailed description, have been achieved by the inventor's discovery that the sarcopenia can be treated with a growth hormone secretagogue.

BRIEF DESCRIPTION OF THE DRAWINGS

FIG. 2A: The bar graphs show mean (±SE) 24-h mean GH levels (μg/L) at baseline, 6 and 12 months; placebo (N=22, red bars) and MK-677 (25 mg p.o. daily) (N=43, green bars). An asterisk indicates a significantly increased fold-change in GH with MK-677 vs. placebo; mean (range) fold-changes with MK-677 treatment were 1.9 (1.6-2.2) and 1.8 (1.6-2.0) at 6 and 12 months, respectively (P<0.001, both time points). The dotted line indicates the median 24-h GH concentration for young adults (for young men and women combined ~1.4 μg/L).

FIG. 2B: Twenty-four hour GH profiles in a 70-year-old man, BMI 23.2 kg/m$^2$, treated for one year with MK-677 (25 mg p.o. daily). Samples were drawn for GH every 10 minutes for 24 h; subjects were allowed to sleep after 21:00. 24-h mean GH levels were 0.37, 1.0 and 0.86 μg/L at baseline (red triangles), 6 months (yellow circles) and 12 months (green circles), respectively. Note the enhanced normal pulsatile pattern which is sustained over 12 months.

FIG. 2C: The bar graphs show mean (±SE) IGF-I levels (μg/L) at baseline, 6 and 12 months; placebo (N=22, red bars) and MK-677 (25 mg p.o. daily) (N=43, green bars). At baseline the treatment groups were not different (P=0.09). An asterisk indicates a significant 1.5-fold increase in IGF-I levels at 6 and 12 months in the MK-677-treated group (P<0.001 vs. placebo, both time points). The dotted line indicates the lower limit of the normal range for young adults aged 21-25 (116-358 μg/L).

FIG. 2D: Mean (±SE) IGF-I levels (μg/L) in the placebo (red triangles) and MK-677 (25 mg p.o. daily) treatment groups (green circles and blue squares) during the 2-year treatment period. Note that IGF-I levels increased into the normal range for young adults aged 21-25 (116-358 μg/L) in the first year. This effect persisted in individuals who were treated with MK-677 for 2 years (green circles, N=20) and those switched from placebo to MK-677 (red triangles, N=20) had a similar increase in year two; crossover to placebo (blue squares) resulted in a return to baseline levels (N=19). At the end of the 2 year study those subjects still on MK-677 were withdrawn from medication and serum IGF-I levels fell to baseline levels at both 3 and 6 months following withdrawal of Mk-677.

FIG. 3A: The bar graphs show the changes (mean difference (±SE)) from baseline at 12 months in total body weight (kg), total fat mass (kg) measured by 4-compartment (4-C) model and DXA methods, and abdominal visceral fat (AVF) (cm$^2$) measured by CT; placebo (N=22, light blue bars) and MK-677 (25 mg p.o. daily) (N=43, dark blue bars). The change in weight with MK-677 was significantly different from placebo (P±0.003). Total body fat mass was significantly increased in both treatment groups, however, there was no significant difference between groups (P=0.1). Subcutaneous fat was significantly increased from baseline in the MK-677 group (P<0.001); vs. placebo (P=0.054). AVF was significantly increased with MK-677 (P=0.02), but this was not different from placebo (P=0.7)

FIG. 3B: The bar graphs show the changes [mean difference (±SE)] from baseline in fat-free mass (FFM) measured by 4-compartment (4-C) model and DXA methods and total appendicular skeletal (lean) mass (Total ASM); placebo (N=22, light blue bars) and MK-677 (25 mg p.o. daily) (N=43, dark blue bars). Total ASM is the sum of lean mass in all 4 limbs derived from the DXA whole body scan. The increase in FFM with MK-677 was significantly different from baseline (P<0.001) and compared to placebo (P≦0.001); this increase was observed by two different methods (4-C and DXA) at both 6 and 12 months. Total ASM was also significantly increased from baseline at 6 and 12 months (P≦0.001) and vs. placebo (P<0.001). Leg ASM was significantly increased from baseline and vs. placebo (P=0.001). However, with MK-677 the small increase in thigh muscle area measured by CT did not reach statistical significance (P=0.2 vs. placebo).

FIG. 3C: The bar graphs show the changes [mean difference (±SE)] from baseline. For analysis, each body water variable (kg) was expressed per kg FFM at each time point, e.g., TBW/FFM. Total body water was determined by deuterium dilution, ECW by bromide dilution and ICW was assessed as the difference between TBW and ECW. The ratios of total body water (TBW/FFM), extracellular water (ECW/FFM) and intracellular water (ICW/FFM) at 12 months are shown in placebo (N=22, light blue bars) and MK-677-treated (25 mg p.o. daily) (N=43, dark blue bars) groups. There were no significant changes in TBW, ECW or ICW with MK-677 treatment vs. placebo. However, during one year of placebo, there was an absolute loss of cell mass (ICW) that is reflected in a loss of total FFM, specifically TASM (FIG. 3B). With placebo, the relatively greater loss of cell mass, and greater expansion of ECW than FFM, is reflected in the corresponding directions of ratios; ICW/FFM (P=0.2) and ECW/FFM (P=0.03) vs. baseline. During one year of MK-677 treatment, these effects not only were prevented, they appear to be partially reversed, with an increase in absolute ICW at 12 months and FFM (FIG. 3B), and an increase in ICW/FFM (P=0.2 vs. placebo) and related TBW/FFM (P=0.004 vs. baseline, P=0.3 vs. placebo).

FIG. 5: T-scores for total appendicular skeletal (lean) mass [TASM (kg)/ht$^2$ (m$^2$)] were computed for each individual based on gender-specific young adult mean and SD values for TASM/ht$^2$ from Gallagher et al. (12)(see Example 2). Total ASM is the sum of lean mass in all 4 limbs derived from the DXA whole body scan at each time point. Individual t-scores at baseline (open circles) and after 12 months of treatment (closed circles) are shown for placebo (N=22, red circles, FIG. 5A) and MK-677 (25 mg p.o. daily), (N=43, green circles, FIG. 5B). T-scores were significantly increased with MK-677 vs. placebo (P<0.001). According to Baumgartner et al. (13;14)(see Example 2) sarcopenia was defined as a t-score≦2 SD below the young, gender-specific reference population. At the end of year 1, the t-score did not change or declined in 17 of 22 subjects on placebo (FIG. 5A); in the MK-677 group (FIG. 5B), 26 of 43 (60%) had an increase and only 7 of 43 had a decrease in t-score (P<0.001 vs. placebo).

DETAILED DESCRIPTION

Figure 1:
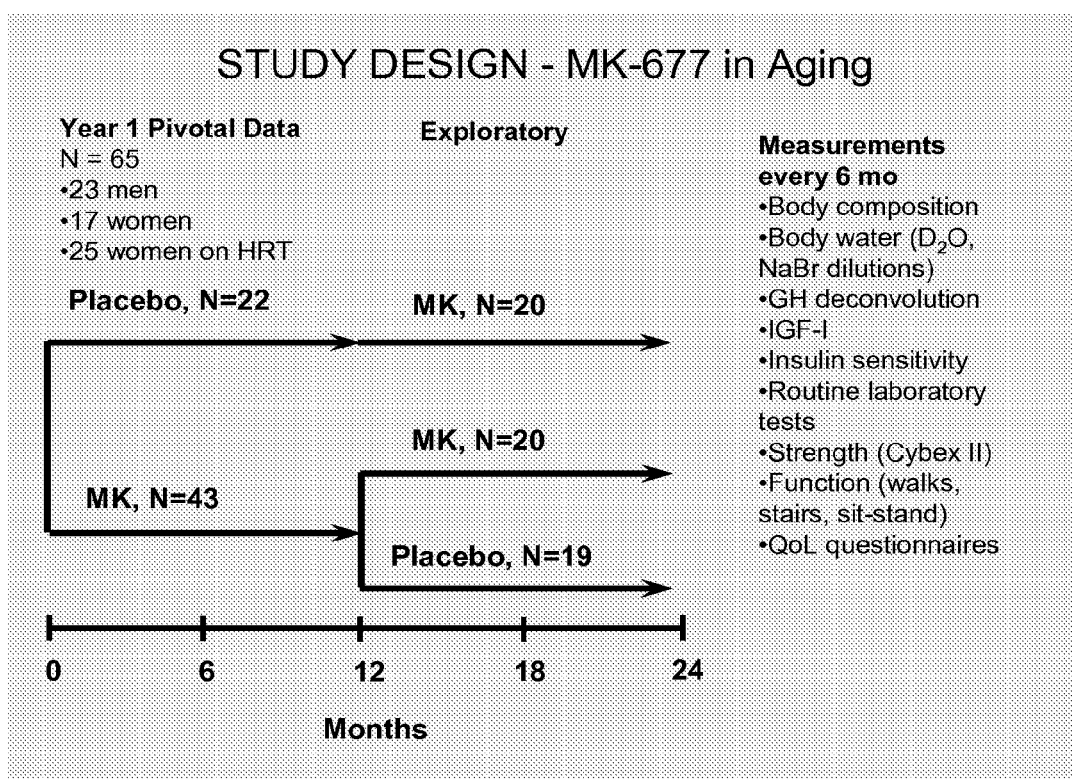
FIG. 1: A schematic of the study design and details of subject inclusion/exclusion criteria, screening, enrollment, and attrition are shown.

The present invention is based on the unexpected finding that Ibutamoren mesylate (MK-677), a growth hormone secretagogue, is capable of preventing the progression of and even partially reversing sarcopenia. This finding was unexpected because it was not previously known that growth hormone secretagogues were useful in treating sarcopenia.

An example of such a treatment is the administration of 25 mg orally of MK-0677 daily, which has been found to increase GH secretion to that observed in young adults, increase IGF-1 levels, and increase appendicular skeletal muscle by 1.6 kg compared to placebo over the first year. This effect was maintained for as long as treatment was continued, but disappeared when the treatment was stopped.

Thus, in an embodiment, the present invention provides a novel method of maintaining or increasing muscle mass to treat sarcopenia, comprising: administering to a patient in need thereof a therapeutically effective amount of a growth hormone secretagogue.

Sarcopenia, as defined by Baumgartner, is the appendicular skeletal muscle mass (kg/height$^2$ (m$^2$)) being less than two standard deviations below the mean of a young reference group (i.e., the t-score). A t-score is determined by measuring the axial skeletal muscle mass of a patient, typically by dxa (i.e., dual energy xray absorptiometry) or a similar and reproducible measure. The measurement of axial skeletal muscle mass can be used to follow the progress of the patient to determine if treatment is slowing, preventing, or reversing muscle mass decline.

Treating sarcopenia (or to treat sarcopenia) includes slowing its progression, stopping its progression, and partially reversing it. An example of slowing the progression of sarcopenia would be to change the length of time a patient would go from a t-score of −1.5 to −2 (e.g., if such a progression would normally take 5 years, then treating as used herein could slow this change to 10 years). Examples of partial reversal include reducing a t-score 0.1, 0.2, 0.3, 0.4, 0.5, 0.6, 0.7, 0.8, 0.9, 1.0 or more units (e.g., moving from a t-score of −2 to a t-score of −1.9, −1.8, −1.7, −1.6, −1.5, −1.4, −1.3, −1.2, −1.1, etc.). Treating sarcopenia also includes delaying the onset of sarcopenia. For example, if a typical male age 50 would begin to see signs of sarcopenia by age 55, treatment according to the present invention could delay the onset 1, 2, 3, 4, 5, 6, 7, 8, 9, 10, or more years. Thus, treating sarcopenia would include treating patients who have not yet been diagnosed with sarcopenia, but who would be vulnerable or expected to be vulnerable to developing sarcopenia. Patients who are vulnerable or expected to be vulnerable also include (a) patients using glucocorticoid steroids, (b) patients with chronic infections, (c) patients with chronic inflammatory conditions (e.g., inflammatory bowel disease), and (d) patients with cancer.

Another type of patient that would benefit from the present invention is one that has suffered some loss of muscle mass, but who does not suffer from a condition that interferes with acts of daily living and/or prevents the subject from living an independent life (e.g., a patient who might soon need assisted living).

In another embodiment, a further decline in t-score is prevented via treatment for at least a year.

In another embodiment, an increase in the t-score of patient is obtained via treatment for at least a year.

In another embodiment, the growth hormone secretagogue is Ibutamoren mesylate (MK-677)(N-[1(R)-[(1,2-dihydro-1-methanesulfonylspiro[3H-indole-3,4'-piperidin]-1'-y l)carbonyl]-2-(phenylmethyloxy)ethyl]-2-amino-2-methylpropanamide methanesulfonate).

Examples oft-scores include 3, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, 0.1, 0, −0.1, −0.2, −0.3, −0.4, −0.5, −0.6, −0.7, −0.8, −0.9, −1.0, −1.1, −1.2, −1.3, −1.4, −1.5, −1.6, −1.7, −1.8, −1.9, −2.0, −2.1, −2.2, −2.3, −2.4, −2.5, −2.6, −2.7, −2.8, −2.9, −3.0, −3.1, −3.2, −3.3, −3.4, −3.5, −3.6, −3.7, −3.8, −3.9, −4.0, −4.1, −4.2, −4.3, −4.4, −4.5, −4.6, −4.7, −4.8, −4.9, −5.0, −5.1, −5.2, −5.3, −5.4, −5.5, −5.6, −5.7, −5.8, −5.9, and −6.0. Typically patients with negative t-scores are more likely to be treated for sarcopenia. However, a patent that is at risk of losing function or who has a medical need to maintain muscle may also be a subject for treatment in accordance with the present invention even if their t-score is 0 or greater.

In another embodiment, the patient has a t-score selected from (a)≦−3, (b)≦−2.5 (c), ≦−2, (d)≦−1.5, (e)≦−1.0, and (f)≦−0.5.

The age or age range of the patient can vary depending on their susceptibility to sarcopenia. Examples of ages and age ranges include (a) 40-45, (b) 45-50, (c) 50-55, (d) 55-60, (e) 60-65, (f) 65-70, (g) 70-75, (h) 75-80, (i) 80-85, (j) 85-90, or older.

In another embodiment, the age of the patient is selected from at least (a) 40, (b) 50, (c) 55, (d) 60, (e) 65, and (f) 70.

In another embodiment, the present invention provides a novel method of maintaining or increasing muscle mass to treat sarcopenia, comprising: administering to a patient in need thereof a therapeutically effective amount of a pharmaceutical composition, comprising a growth hormone secretagogue and a pharmaceutically acceptable carrier.

One of ordinary skill in the art will recognize that the dosage or dosages chosen for a growth hormone secretagogue will depend on the specific secretagogue. Thus, a range of doses of growth hormone secretagogue (e.g., Ibutamoren mesylate (MK-677)) may be useful. Ranges may include (a) up to 1000 mg p.o. daily, (b) up to 500 mg p.o. daily, (c) up to 100 mg p.o. daily, (d) up to 25 mg p.o. daily, and (e) up to 10 mg p.o. daily. In some cases administration other than p.o. may be useful. The administration of the growth hormone secretagogue can be done other that once per day, and could include different doses multiple times per day, or even less than once per day. Other types of drugs such as anabolic drugs also may be administered to the subjects in addition to the growth hormone secretagogue, depending on the treatment desired.

"Growth hormone secretagogue" refers to any compound or agent that binds to and stimulates the growth hormone secretagogue receptor 1a and acts a mimetic of ghrelin. Growth hormone secretagogue includes any exogenously administered compound or agent that directly or indirectly stimulates or increases the endogenous release of growth hormone, growth hormone-releasing hormone, or somatostatin in an animal, in particular, a human. The growth hormone secretagogue may be peptidal or non-peptidal in nature. An orally active growth hormone secretagogue is typically desirable. In addition, it is desirable that the growth hormone secretagogue induces or amplifies a pulsatile release of endogenous growth hormone.

The growth hormone secretagogue may be used alone or in combination with other growth hormone secretagogues or with other agents which are known to be beneficial for enhancing the return of patients to independent living status following deconditioning. The growth hormone secretagogue and the other agent may be co-administered, either in concomitant therapy or in a fixed combination. For example, the growth hormone secretagogue may be administered in combination with other compounds which are known in the art to be useful for enhancing the return of patients to independent living status following deconditioning.

Representative growth hormone secretagogues are disclosed in: U.S. Pat. Nos. 3,239,345; 4,036,979; 4,411,890; 5,206,235; 5,283,241; 5,284,841; 5,310,737; 5,317,017; 5,374,721; 5,430,144; 5,434,261; 5,438,136; 5,494,919; 5,494,920; 5,492,916; 5,536,716; 6,194,402; U.S. Patent Application Publication No. 2002/0028838; EPO Patent Pub. No. 0,144,230; EPO Patent Pub. No. 0,513,974; PCT Patent Pub. No. WO 89/07110; PCT Patent Pub. No. WO 89/07111; PCT Patent Pub. No. WO 93/04081; PCT Patent Pub. No. WO 94/07486; PCT Patent Pub. No. WO 94/08583; PCT Patent Pub. No. WO 94/11012; PCT Patent Pub. No. WO 94/13696; PCT Patent Pub. No. WO 94/19367; PCT Patent Pub. No. WO 95/03289; PCT Patent Pub. No. WO 95/03290; PCT Patent Pub. No. WO 95/09633; PCT Patent Pub. No. WO 95/11029; PCT Patent Pub. No. WO 95/12598; PCT Patent Pub. No. WO 95/13069; PCT Patent Pub. No. WO 95/14666; PCT Patent Pub. No. WO 95/16675; PCT Patent Pub. No. WO 95/16692; PCT Patent Pub. No. WO 95/17422; PCT Patent Pub. No. WO 95/17423; PCT Patent Pub. No. WO 95/34311; PCT Patent Pub. No. WO 96/02530; PCT Patent Pub. No. WO 96/05195; PCT Patent Pub. No. WO 96/15148; PCT Patent Pub. No. WO 96/22782; PCT Patent Pub. No. WO 96/22997; PCT Patent Pub. No. WO 96/24580; PCT Patent Pub. No. WO 96/24587; PCT Patent Pub. No. WO 96/35713; PCT Patent Pub. No. WO 96/38471; PCT Patent Pub. No. WO 97/00894; PCT Patent Pub. No. WO 97/06803; PCT Patent Pub. No. WO 97/07117; J. Endocrinol Invest., 15(Suppl 4), 45 (1992)); Science 260, 1640-1643 (Jun. 11, 1993); Ann. Rep. Med. Chem., 28, 177-186 (1993); Bioorg. Med. Chem. Ltrs., 4(22), 2709-2714 (1994); and Proc. Natl. Acad. Sci. USA 92, 7001-7005 (July 1995).

Some representative compounds include:
1) N-[1(R)-[(1,2-Dihydro-1-methanesulfonylspiro[3H-indole-3,4'-piperidin]-1'-yl)carbonyl]-2-(1H-indol-3-yl) ethyl]-2-amino-2-methylpropanamide;
2) N-[1(R)-[(1,2-Dihydro-1-methanecarbonylspiro[3H-indole-3,4'-piperidin]-1'-yl)carbonyl]-2-(1H-indol-3-yl) ethyl]-2-amino-2-methylpropanamide;
3) N-[1(R)-[(1,2-Dihydro-1-benzenesulfonylspiro[3H-indole-3,4'-piperidin]-11'-yl)carbonyl]-2-(1H-indol-3-yl) ethyl]-2-amino-2-methylpropanamide;
4) N-[1(R)-[(3,4-Dihydro-spiro[2H-1-benzopyran-2,4'-piperidin]-1'-yl)carbonyl]-2-(1H-indol-3-yl)ethyl]-2-amino-2-methylpropanamide;
5) N-[1(R)-[(2-Acetyl-1,2,3,4-tetrahydrospiro[isoquinolin-4,4'-piperidin]-1'-yl)carbonyl]-2-(indol-3-yl)ethyl]-2-amino-2-methyl-propanamide;
6) N-[1(R)-[(1,2-Dihydro-1-methanesulfonylspiro[3H-indole-3,4'-piperidin]-1'-yl)carbonyl]-2-(phenylmethyloxy) ethyl]-2-amino-2-methylpropanamide;
7) N-[1(R)-[(1,2-Dihydro-1-methanesulfonylspiro[3H-indole-3,4'-piperidin]-1'-yl)carbonyl]-2-(phenylmethyloxy) ethyl]-2-amino-2-methylpropanamide mesylate salt;
8) N-[1(R)-[(1,2-Dihydro-1-methanesulfonylspiro[3H-indole-3,4'-piperidin]-1'-yl)carbonyl]-2-(2',6'-difluorophenylmethyloxy)ethyl]-2-amino-2-methylpropan amide;
9) N-[1(R)-[(1,2-Dihydro-1-methanesulfonyl-5-fluorospiro [3H-indole-3,4'-piper idin]-1'-yl)carbonyl]-2-(phenylmethyloxy)ethyl]-2-amino-2-methylpropanamide;
10) N-[1(S)-[(1,2-Dihydro-1-methanesulfonylspiro[3H-indole-3,4'-piperidin]-11'-yl)carbonyl]-2-(phenylmethylthio)ethyl]-2-amino-2-methylpropanamide;
11) N-[1(R)-[(1,2-Dihydro-1-methanesulfonylspiro[3H-indole-3,4'-piperidin]-1'-yl)carbonyl]-3-phenylpropyl]-2-amino-2-methylpropanamide;
12) N-[1(R)-[(1,2-Dihydro-1-methanesulfonylspiro[3H-indole-3,4'-piperidin]-1'-yl)carbonyl]-3-cyclohexylpropyl]-2-amino-2-methylpropanamide;
13) N-[1(R)-[(1,2-Dihydro-1-methanesulfonylspiro[3H-indole-3,4'-piperidin]-1'-yl)carbonyl]-4-phenylbutyl]-2-amino-2-methylpropanamide;
14) N-[1(R)-[(1,2-Dihydro-1-methanesulfonylspiro[3H-indole-3,4'-piperidin]-1'-yl)carbonyl]-2-(5-fluoro-1H-indol-3-yl)ethyl]-2-amino-2-methylpropanamide;
15) N-[1(R)-[(1,2-Dihydro-1-methanesulfonyl-5-fluorospiro[3H-indole-3,4'-piper idin]-1'-yl)carbony]-2-(5-fluoro-1H-indol-3-yl)ethyl]-2-amino-2-methylpropa namide;
16) N-[1(R)-[(1,2-Dihydro-1-(2-ethoxycarbonyl)methylsulfonylspiro-[3H-indole-3,4'-piperidin]-1'-yl)carbonyl]-1-(1H-indol-3-yl)ethyl]-2-amino-2-methylprop anamide;
17) N-[1(R)-[(1,2-Dihydro-1,1-dioxospiro[3H-benzothiophene-3,4'-piperidin]-1'-yl)carbonyl]-2-(phenylmethyloxy)ethyl]-2-amino-2-methylpropanamide;
and pharmaceutically acceptable salts thereof.

Unless otherwise defined, all technical and scientific terms used herein have the same meaning as commonly understood by one of ordinary skill in the art to which this invention belongs. Although any materials and methods similar or equivalent to those described herein can be used in the practice or testing of the present invention, the preferred materials and methods are described herein. As used herein, each of the following terms has meaning associated with it in this section. Specific and preferred values listed below for radicals, substituents, and ranges are for illustrations only; they do not exclude other defined values or other values within defined ranges for the radicals and substituents. Patient includes warm blooded mammals that are typically under medical care (e.g., humans and domesticated animals). Examples of mammals include (a) feline, canine, equine, bovine, porcine and human and (b) human.

The articles "a" and "an" are used herein to refer to one or to more than one (i.e., to at least one) of the grammatical object of the article. By way of example, "an element" means one element or more than one element.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, p 1445, the disclosure of which is hereby incorporated by reference.

As used herein, an "effective amount" means an amount sufficient to produce a selected or desired effect.

As used herein, a "functional" molecule is a molecule in a form in which it exhibits a property by which it is characterized. By way of example, a functional enzyme is one which exhibits the characteristic catalytic activity by which the enzyme is characterized.

The term "inhibit," as used herein, refers to the ability of a compound of the invention to reduce or impede a described function. Preferably, inhibition is by at least 10%, more preferably by at least 25%, even more preferably by at least 50%, and most preferably, the function is inhibited by at least 75%.

As used herein, an "instructional material" includes a publication, a recording, a diagram, or any other medium of expression which can be used to communicate the usefulness of the growth hormone secretagogue of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

The term, "parenteral" means not through the alimentary canal but by some other route such as subcutaneous, intramuscular, intraspinal, or intravenous.

As used herein, the term "pharmaceutically acceptable carrier" includes any of the standard pharmaceutical carriers, such as a phosphate buffered saline solution, water and emulsions such as an oil/water or water/oil emulsion, and various types of wetting agents. The term also encompasses any of the agents approved by a regulatory agency of the US Federal government or listed in the US Pharmacopeia for use in animals, including humans.

As used herein, the term "purified" and the like terms relate to the isolation of a molecule or compound in a form that is substantially free (at least 60% free, preferably 75% free, and most preferably 90% free) from other components normally associated with the molecule or compound in a native environment. The term "purified" does not necessarily indicate that complete purity of the particular molecules achieved during the process. A "highly purified" compound as used herein refers to a compound that is greater than 90% pure.

A "sample," as used herein, refers preferably to a biological sample from a subject, including, but not limited to, normal tissue samples, diseased tissue samples, biopsies, blood, saliva, feces, semen, tears, and urine. A sample can also be any other source of material obtained from a subject that contains cells, tissues, or fluid of interest. A sample can also be obtained from cell or tissue culture.

The term "standard," as used herein, refers to something used for comparison. For example, a standard can be a known standard agent or compound which is administered or added to a control sample and used for comparing results when measuring said compound in a test sample. Standard can also refer to an "internal standard," such as an agent or compound which is added at known amounts to a sample and is useful in determining such things as purification or recovery rates when a sample is processed or subjected to purification or extraction procedures before a marker of interest is measured.

A "subject" of analysis, diagnosis, or treatment is an animal. Such animals include mammals, preferably a human.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

The active ingredient of the pharmaceutical compositions of the present invention can comprise a growth hormone secretagogue and an anabolic agent or another agent which exhibits a different activity, e.g., an antibiotic growth promoting agent, a corticosteroid to minimize catabolic side effects or another pharmaceutically active material wherein the combination enhances efficacy and/or minimizes side effects, if any.

Also, the present invention includes within its scope the use of a growth hormone secretagogue according to the present invention, alone or in combination with a naturaceutic, a prodrug thereof, or a pharmaceutically acceptable salt of said naturaceutic or said prodrug. A naturaceutic is typically an over-the-counter composition that is promoted as, for example, improving health or general well-being. It includes compositions such as vitamins, dietary supplements, creatine, creatine phosphate, and amino acids such as L-arginine.

The invention further provides a kit. An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably, the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the dosage form so specified should be ingested. Another example of such a memory aid is a calendar printed on the card e.g., as follows "First Week, Monday, Tuesday, etc. Second Week, Monday, Tuesday," etc. Other variations of memory aids will be readily apparent. A "daily dose" can be a single tablet or capsule or several tablets or capsules to be taken on a given day. Also, a daily dose of a second therapeutic agent as described herein can consist of one tablet or capsule while a daily dose of the growth hormone secretagogue, prodrug thereof or pharmaceutically acceptable salt of said growth hormone secretagogue or said prodrug can consist of several tablets or capsules or vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter, which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

In view of their use according to the present invention, the growth hormone secretagogues of the present invention may be formulated into various pharmaceutical forms for administration purposes. A growth hormone secretagogue may be administered, alone or in combination, by oral, parenteral (e.g., intramuscular, intraperitoneal, intravenous or subcutaneous injection, or implant), nasal, vaginal, rectal, sublingual, or topical routes of administration and can be formulated with pharmaceutically acceptable carriers to provide dosage forms appropriate for each route of administration.

Solid dosage forms for oral administration include capsules, tablets, pills, powders, and granules and for companion animals, the solid dosage forms include an admixture with food and chewable forms. In such solid dosage forms, the compounds and combinations of this invention can be admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings. In the case of chewable forms, the dosage form may comprise flavoring agents and perfuming agents.

Liquid dosage forms for oral administration include pharmaceutically acceptable emulsions, solutions, suspensions, syrups, and elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions, which can be dissolved in sterile water, or some other sterile injectable medium immediately before use.

Compositions for rectal or vaginal administration are preferably suppositories, which may contain, in addition to a compound of the present invention, excipients such as cocoa butter or a suppository wax. Compositions for nasal or sublingual administration are also prepared with standard excipients well known in the art.

Where the tartrate salt or other pharmaceutically acceptable salt of a compound of the present invention is used, the skilled person will be able to calculate effective dosage amounts by calculating the molecular weight of the salt form and performing simple stoichiometric ratios.

In accordance with the present invention, as described above or as discussed in the Examples below, there can be employed conventional chemical, cellular, histochemical, biochemical, molecular biology, microbiology, and in vivo techniques which are known to those of skill in the art. Such techniques are explained fully in the literature.

Without further description, it is believed that one of ordinary skill in the art can, using the preceding description and the following illustrative examples, make and utilize the present invention. The following working examples therefore, are provided for the purpose of illustration only and specifically point out the preferred embodiments of the present invention, and are not to be construed as limiting in any way the remainder of the disclosure. Therefore, the examples should be construed to encompass any and all variations which become evident as a result of the teaching provided herein.

EXAMPLES

The results described herein have never been demonstrated in man and in view of the modest increase in growth hormone and IGF-I levels this finding is surprising. That one tablet a day in older subjects could achieve this outcome is remarkable particularly in view of the lack of serious adverse effects. This observation could have a marked impact on the quality of life and cost of health care for the burgeoning older population as the 'baby boomers' now reach this stage in life.

Example 1

It has been previously reported that treatment of healthy older men and women with the orally active GH secretagogue Ibutamoren mesylate (MK-677, 25 mg p.o. daily) enhanced IGF-I and pulsatile GH release into the young adult normal range, without the side effects associated with GH therapy (1). This example presents the 6 and 12 mo (pivotal) body composition data in all subjects studied in a 2-yr crossover study. A total of 65 healthy older [60-81 yr; BMI 26.1±3 (19-35) kg/m$^2$] men and women on and off HRT (hormone replacement therapy) received MK-677 (⅔ of each group) or placebo in Yr 1. Total body fat mass, % fat, and fat-free mass (FFM) were determined every 6 mo over 2 yr using a 4-compartment (4-C) model, as well as dual energy x-ray absorptiometry (DXA, QDR 2000). 4-C model components: body weight and density (BodPod); total body water (D$_2$O dilution); total bone mineral content (DXA). Data were analyzed by way of repeated measure ANCOVA with baseline response as the model covariate. P values and confidence limits were derived based on a Bonferroni two-sided experiment wise error rate 0.05; data shown are mean (upper and lower Bonferroni 95% CL).

| | | Mean Change in FFM (kg) from Baseline | |
|---|---|---|---|
| | | Placebo (n = 22) | MK-677 (n = 43) |
| 4-C | 6 mo | −0.16 (−1.03-0.72) | 1.12 (0.48-1.75) |
| DXA | 6 mo | −0.17 (−0.87-0.54) | 0.98 (0.47-1.48) |
| 4-C | 12 mo | −0.36 (−1.23-0.52) | 1.27 (0.64-1.90) |
| DXA | 12 mo | −0.45 (−1.16-0.25) | 1.09 (0.58-1.59) |

| Estimated Difference in Change (MK-677 vs Placebo) | | | | |
|---|---|---|---|---|
| | | FFM | | Body Wt |
| 4-C | 6 mo | 1.28 (0.21-2.36)* | 6 mo | 2.3 (0.8-3.8)*** |
| DXA | 6 mo | 1.15 (0.28-2.02)** | | |
| 4-C | 12 mo | 1.64 (0.56-2.71)** | 12 mo | 1.9 (0.5-3.4)** |
| DXA | 12 mo | 1.54 (0.67-2.41)*** | | |

$P < 0.05$,
**$P < 0.01$,
***$P < 0.001$.

MK-677 treatment of healthy older adults significantly increased body weight and FFM (by 4-C and DXA) at 6 and 12 mo when compared to placebo. The increase in total body fat and % fat in both the placebo and MK-677 groups were not significantly different.

Yr 2 descriptive data: In subjects who were treated with MK-677 for 2 yr (n=17), the increase in FFM in the first year was maintained; in those who were switched from MK-677 to placebo in yr 2, the observed increase in FFM was lost, and in fact, declined. It is well established that sarcopenia correlates with frailty and its implications (2). Administration of an orally-active GH secretagogue that slows or prevents sarcopenia potentially improves the outlook for the aging population. Further correlation with functional studies will be important.

Bibliography for Example 1.

(1) Nass et al., Endocrine Society Meeting, San Diego, 2005 (OR33-6).

(2) Fried et al., J Gerontology: Med Sci 2001, 56A:M146-M156.

Example 2

Methods

Sixty-five healthy men and women (±HRT) ages 60-81 years were enrolled in a 2-year study of MK-677 (25 mg p.o. daily) or placebo. In addition to GH and IGF-I, the primary endpoints were fat-free mass (FFM), by 4-compartment model and DXA, and abdominal visceral fat (AVF) by CT. Secondary endpoints included isokinetic strength, function and quality of life (QoL); all endpoints were assessed at baseline and every 6 months, with frequent monitoring for adverse effects.

Summary of Results

Daily MK-677 significantly increased pulsatile GH and IGF-I levels to those of normal young adults without serious side effects. Body weight and FFM increased significantly compared to placebo, with no change in AVF or fat mass. Increased FFM did not result in changes in function or QoL. However, with MK-677 treatment there was a trend (P=0.07) for prevention of the decline in shoulder flexion strength observed in those treated with placebo.

Conclusions

GH secretion can be restored safely in this population with orally-active MK-677 (ghrelin mimetic). The sarcopenia of aging can be slowed and even reversed by increasing GH secretion in a physiologic manner, having potentially important personal, economic, and social implications.

Subjects

Healthy men and women 60 years and older were eligible to participate. A schematic of the study design and details of subject inclusion/exclusion criteria, screening, enrollment, and attrition are shown in FIG. 1. Volunteers were carefully screened by medical history and physical examination to rule out underlying disease and extensive laboratory testing was performed before and frequently throughout the study. Participants were asked to maintain their typical diet and exercise throughout the study and to report any illnesses, medical procedures or side effects. Annual mammograms and pap smears were performed in women and levels of prostate-specific antigen (PSA) were monitored in men.

Study Design

This NIH-funded study was approved by the General Clinical Research Center (GCRC) and the University of Virginia Institutional Review Boards. All subjects gave written informed consent. A two-year, double-blind, placebo-controlled modified crossover trial of once-daily administration of an oral GH secretogogue (MK-677, 25 mg) to healthy older adults was performed.

During the first year, subjects were randomized to MK-677 or placebo treatment. In each of 3 groups (23 men, 25 women on hormone replacement therapy (HRT) and 17 women not on HRT), ⅔ received MK-677 and ⅓ received placebo. At the end of year 1, the subjects who received placebo were switched to MK-677 treatment (N=⅔ in year 2); subjects who received MK-677 for the first year were randomized to continue MK-677 (N=20) or to placebo (N=19).

The study was powered for the pivotal first 12 months based on the primary endpoints of AVF and FFM, with data from men and women combined; effects of year 2 treatment, gender and estrogen status are considered exploratory data and are not reported in detail.

At baseline and every 6 months for 2 years, subjects were admitted to the GCRC for body composition and body water measurements, frequent blood sampling and completion of quality of life questionnaires; tests of strength and function also were performed every 6 months.

Growth hormone (GH) concentrations and pulsatile characteristics. Blood samples were obtained every 10 minutes for 24 hours for measurement of GH in a sensitive chemiluminescence assay (2); endogenous GH secretory dynamics were assessed using an automated multiple-parameter deconvolution method as previously reported (1;3).

Assays and Insulin Sensitivity. Plasma glucose was measured on a Beckman analyzer and insulin and total IGF-I were measured in the GCRC Core Laboratory on an Immulite 2000 (Diagnostic Products Corporation, Los Angeles, Calif.). Additional safety laboratory tests were performed by standard methods in the UVA Clinical Laboratories. Fasting insulin and glucose were used to estimate insulin sensitivity by the Quicki method (4).

Body Composition. The effects of treatment on FFM and total body fat were evaluated by two independent methods: a 4-compartment (4-C) model (5); and dual x-ray absorptiometry (DXA). All subjects were scanned on the same Hologic QDR-2000 in pencil beam mode as previously described (6); all scans were read by a single observer (J. L. C.). Total appendicular skeletal muscle (lean) mass (TASM) from DXA was measured as the sum of the lean soft-tissue masses for the arms and the legs as described by Heymsfield et al. (7). Total and abdominal visceral fat (AVF), and subcutaneous fat areas ($cm^2$), as well as thigh muscle were measured by computed tomography (CT) ((8) and all scans were read by a single observer (J. L. C.)

Body Water. Total body water (TBW) was measured using the deuterium oxide ($D_2O$) dilution technique ((8) and extracellular water (ECW) by bromide dilution (10). Intracellular water (ICW) was assessed as the difference between TBW and ECW. To determine the relative relationships of total-, extra- and intra-cellular water, each component (in kg) was expressed per kg of FFM at each time point.

Quality of Life Assessments. Subjects completed 4 questionnaires to assess quality of life and general well-being: the 20-item Short Form Health Survey (SF-20); Beck Depression Inventory (BDI); Pittsburgh Sleep Quality Index (PSQI); and the Body Cathexis Scale (BCS).

Isokinetic Muscle Strength. Concentric force during flexion and extension of the knee and shoulder were determined using an isokinetic dynamometer Cybex II (CSM, Inc., Boston, Mass.). (11) Six repetitions of maximal effort over 90 degrees at 60 degrees/second were performed with the mean of the last 5 repetitions computed by proprietary software. Total work (Newton metres) was calculated by multiplying the mean per repetition by 5.

Function. Function tests included walking 30 meters as quickly as possible, walking as far as possible in 6 minutes, descending and ascending 4 flights of stairs and rising and sitting 5 times from an armless chair with an 18" seat height.

Correction for Height and Gender. All strength and function measurements were analyzed per kg of skeletal muscle (ASM). Baseline arm ASM and leg ASM were used for shoulder and knee strength, respectively; baseline TASM (sum of arms and legs) was used for the function tests.

Intervention

The PI holds IND # 54,041 for administration of MK-677. MK-677 and placebo tablets and randomizations were kindly provided by Merck Research Laboratories. Randomization included stratification for gender and HRT within each of the 3 treatment groups. The oral dose of MK-677 was 25 mg, taken daily in the morning between 7:00 and 9:00. Ten mg tablets were provided for blind back-titration if needed. All research staff and volunteers remained blinded throughout the study and during data verification; a research pharmacist dispensed the coded study medication which was dispensed at each visit. Compliance was determined by pill count.

Outcome Measures

The primary outcome measures were the effects of increased GH and IGF-I on AVF and FFM; additional outcomes included body weight, fat mass, body water compartments, 24-h GH secretory dynamics, insulin sensitivity, quality of life and physical performance. Because gender and height influence total muscle mass, an index of relative muscle mass was calculated: total ASM from DXA was divided by height squared in meters (TASM $(kg)/ht^2$). To put changes in FFM in a clinical perspective, a t-score was computed for each individual, relating the TASM/$ht^2$ to those of gender-specific young adults (12). In accordance with Baumgartner et al., sarcopenia was defined as $\leq 2$ SD below young, gender-specific reference populations (13; 14).

Monitoring for Adverse Effects

In each of the 2 years, volunteers were seen monthly the first 3 months and every 3 months thereafter for a physical examination, documentation of medications and vital signs, routine laboratory tests and detailed questioning about possible side effects. Fasting blood glucose and hemoglobin A1c (HBA1c) were monitored for possible changes with MK-677 treatment, since increased blood glucose had been observed in previous studies (11;15).

Statistical Analysis

The two primary endpoints for this study are: 1) FFM, which is an important determinant of functional ability; and 2) AVF, which is the most important fat depot for cardiovascular risk. Based on a sample size of 60 subjects (40 randomized to MK-677 and 20 to placebo in year 1), this cross-over study was designed to have at least 90% power to detect a 4.1% or greater between-group difference in the change in percent FFM, with the same power to detect a 12.6% or greater between-group difference in the change in AVF ($cm^2$) after the initial 12-months of treatment. The sample size formula for two-sample Student's t-test was used to conduct the power analysis. The standard deviations used in the power calculations were 4.4% for percent FFM and 14.1% for AVF. Both power calculations reflect the power of a two-sided test with a type I error rate of 0.05.

All statistical analyses were conducted under the guidelines of intention to treat principle. The analyses focused on the baseline and the 6- and 12-month primary and secondary outcomes. The 18- and 24-month data were considered exploratory in nature and were analyzed by way of descriptive statistics.

The primary outcome data for the 6- and 12-month changes in FFM and AVF as well as for IGF-I and GH were analyzed via repeated measures ANCOVA. The FFM and AVF data were analyzed on the same scale as they were measured, while the IGF-I and GH data were transformed to the natural logarithmic scale before conducting the statistical analyses so that the variance and normality assumptions of the linear model were not violated.

For each ANCOVA, two factors were considered as potential sources of variability; treatment assignment (MK-677 or placebo) and measurement assessment time (6- or 12-months). Treatment by time interaction was also considered as a potential source of variability. The subjects' baseline measurements were treated as the ANCOVA covariate.

To estimate the mean within-subject change in the response at 6 and at 12 months, linear contrasts of the least-squares means were constructed. Similarly, we constructed linear contrasts of the baseline-adjusted least-squares means to estimate the baseline-adjusted difference in changes in the response at 6 and 12 months between the MK-677 and placebo groups. For the pivotal 12-month comparison (MK-677 versus placebo), the null hypothesis of equality of means was rejected if the p-value of the F-statistic was less than or equal to 0.05. For the non-pivotal 6-month between-group comparison, the null hypothesis was rejected if the p-value of the F-statistic was less than or equal to 0.05 after implementing the Bonferonni post-hoc test correction. For the 12-months comparison, the 95% confidence interval was constructed based on the t-distribution quantile value at the 97.5 percentile of the distribution, while the 95% confidence interval for the 6-month comparison was constructed based on the t-distribution quantile value at the 98.75 percentile of the distribution.

Since the FFM and AVF data were analyzed on the same scale as initially measured, the 6- and 12-month changes are reported as a difference between arithmetic means; changes in IGF-I and GH data analyzed on the natural algorithmic scale are reported as a ratio of geometric means.

With the exception of the quality of life data, all of the secondary outcome data were analyzed via repeated measure ANCOVA in exactly the same way as the primary outcome data. Changes in secondary outcome data, analyzed on the same scale as initially measured, are reported as a difference between arithmetic means.

With regard to the quality of life data, a Factor Analysis of the different scales of the questionnaires was performed to create an overall well-being factor (16). Initially, study subjects were used as their own internal controls and assessed if there was change over time in overall well being. Using the hierarchical linear modeling (HLM), a growth curve analysis was conducted, testing within-person linear and curvilinear change in overall well being over time.

The software of SAS version 9.1 (SAS Institute Inc, Cary N.C.) was used to conduct the statistical analyses.

Results

Characteristics of the Subjects

Seventy-one subjects were enrolled and treated; results for 65 volunteers who completed year 1 are reported. Details of subject attrition are included in FIG. 1. The treatment groups were well matched, with no statistical difference in any parameter between the MK-677 and placebo groups at baseline.

Forty-one women (25 on HRT, 17 no HRT) and 23 men completed year 1; 53 subjects completed 24 months, and due to expiration of study drug, 5 were treated for only 18 months and one for only 12 months.

24-h mean GH and IGF-I levels

Twenty-four-hour mean GH levels were significantly increased by MK-677 vs. placebo (FIG. 2A); the mean (range) fold-change was 1.9 (1.6-2.2) and 1.8 (1.6-2.0) at 6 and 12 months, respectively (P<0.001). The representative 24-h GH profiles in a 70-year-old man (FIG. 2B), show that the pulsatile pattern of GH secretion at baseline is maintained and enhanced at 6 and 12 months. Deconvolution analysis showed that the increase in GH was primarily a result of increased secretion per peak rather than an increase in peak frequency.

Figure 2:
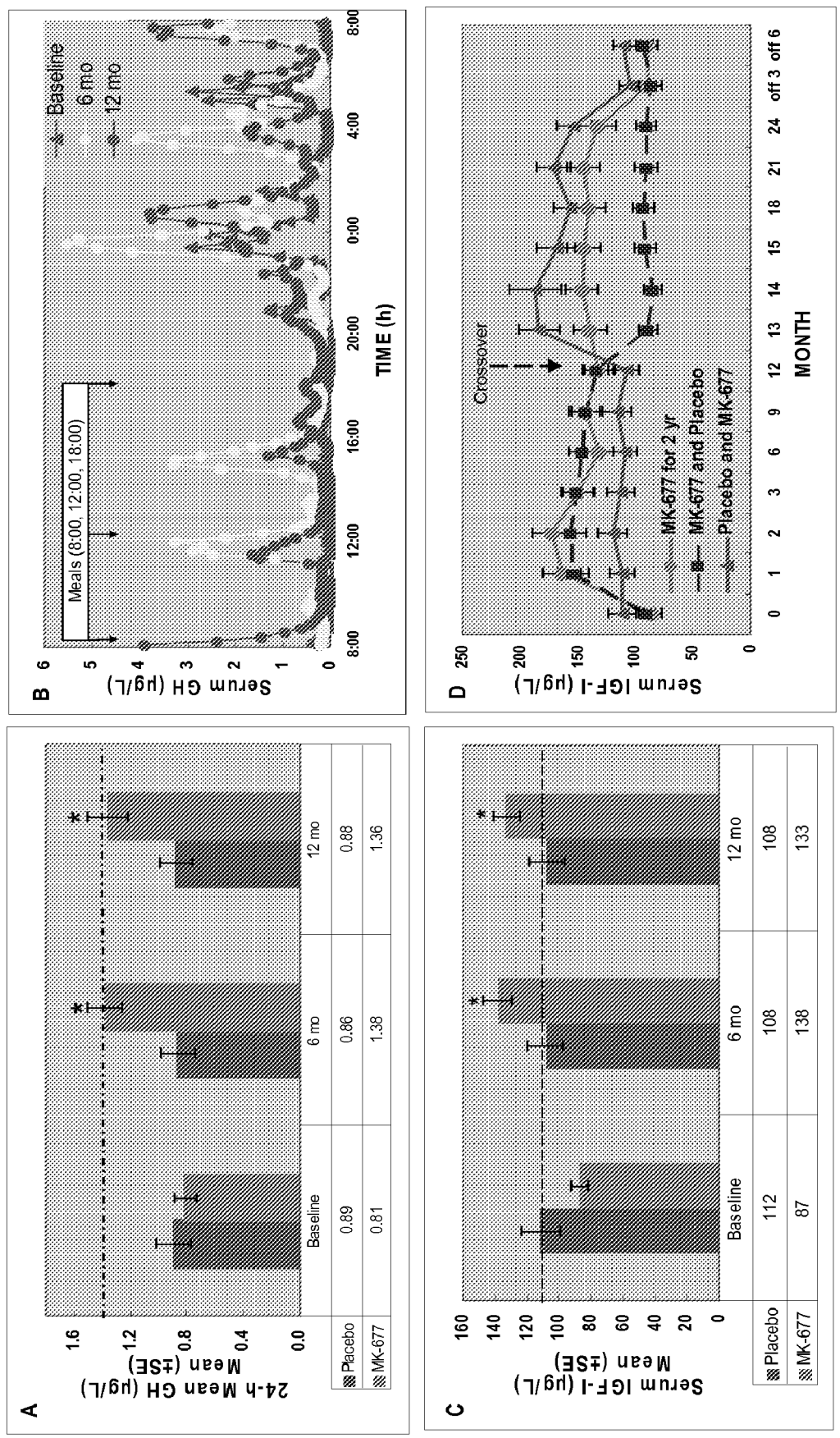
FIG. 2: Serum 24-h mean GH and IGF-I results after one year of treatment. Data were not normally distributed and were analyzed on the natural algorithmic scale and reported as a ratio of geometric means.

Mean IGF-I levels were also enhanced by MK-677 treatment (FIG. 2C) and the 1.5-fold increase at 6 and 12 months was significant vs. placebo (P<0.001). FIG. 2D shows IGF-I responses over 2 years in each of the treatment groups before and after crossover at 12 months. With MK-677 (N=43 in year 1) there was a pronounced increase in serum IGF-I in the first 3 months, with levels in the young adult normal range (21-25 y; 116-358 µg/L) over 12 months. These levels were maintained in those treated for 2 years (N=20). IGF-I returned to pre-treatment levels in subjects switched to placebo after year 1 (N=19).

Body Composition

Figure 3:
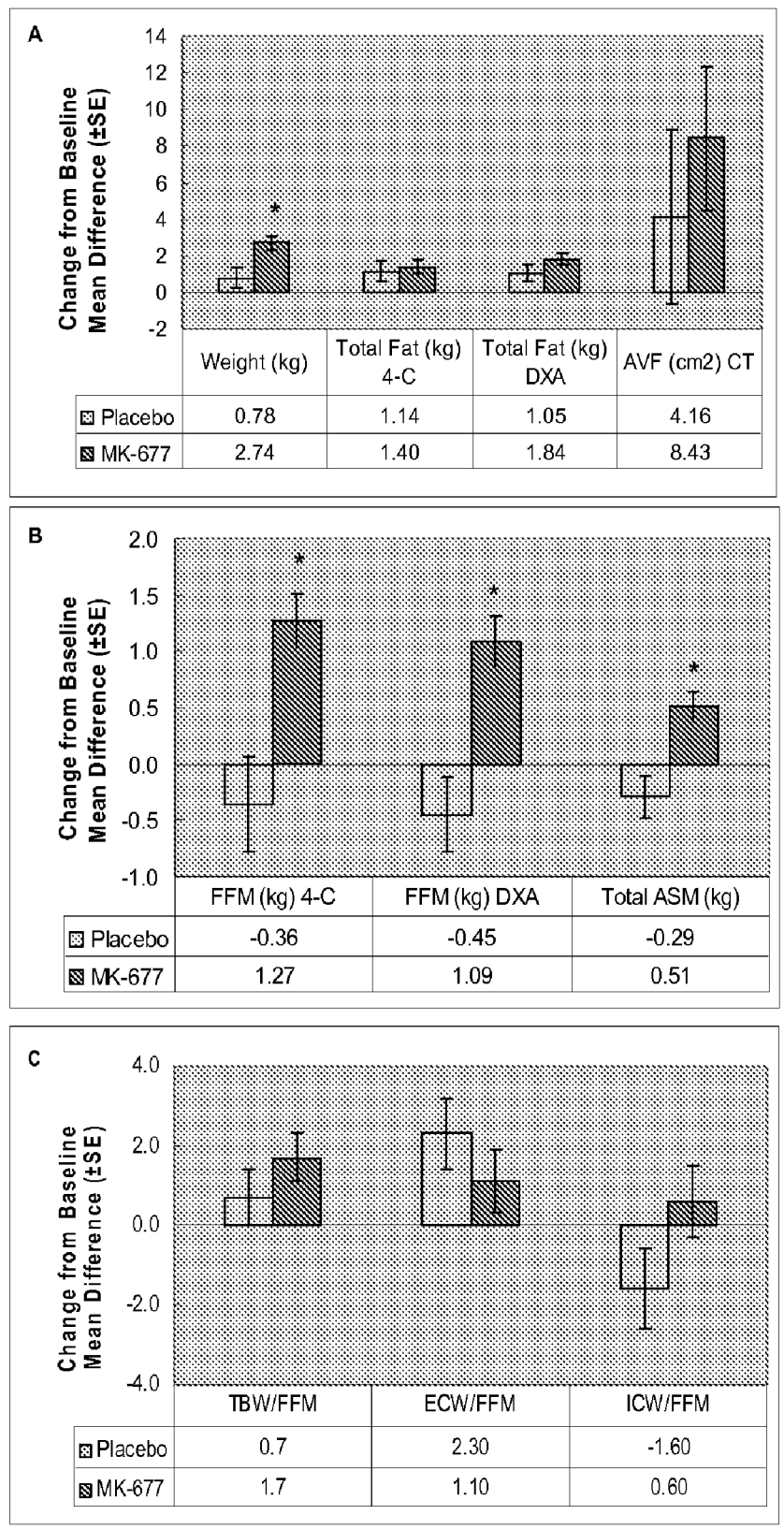
FIG. 3: Body composition and body water results at baseline and after one year of treatment. Data were analyzed on the same scale as initially measured and are reported as a difference between arithmetic means. An asterisk indicates a significant difference vs. placebo at 12 months.

Body Weight (FIG. 3A). Total body weight was significantly increased by MK-677 treatment at 6 months by 3.1 kg vs. 0.7 kg with placebo (P=0.001) and at 12 months by 2.7 kg vs. 0.8 with placebo (P=0.003).

Body Fat (FIG. 3A). When measured by DXA, total body fat at 6 months was increased from baseline in both the placebo group (P=0.06) and the MK-677 group (P<0.001). At 12 months there were statistically significant increases of 1.1 kg (0.2-1.9) in the placebo group (P=0.02) and 1.8 kg (1.2-2.5) in the MK-677 group (P<0.001); however, there was no significant difference between groups (P=0.1). Similar changes were seen at 12 months using the 4-C model.

Abdominal Visceral Fat (FIG. 3A). In the placebo group at 12 months, the mean increase in AVF from baseline was 4.2 $cm^2$ (−6.2-14.5). With MK-677 treatment, the mean AVF increase of 8.4 $cm^2$ (1.6-15.3) was different from baseline (P=0.02), but was not significant vs. placebo (P=0.7).

Fat-free Mass (FFM) and Total Appendicular Skeletal Mass (TASM) (FIG. 3B). There was a significant increase in FFM in the MK-677-treated group when compared to placebo at 6 months (P<0.05) and 12 months (P<0.001). This was found when measured by both DXA and the 4-C model, with a correlation between methods of $r^2$=0.98. With MK-677, the FFM measured by DXA increased 1.1 kg (0.7-1.5), while with placebo FFM decreased 0.5 kg (−1.1-0.2) at 12 months. With the 4-C model the mean changes were similar, with an increase of 1.3 kg (0.7-1.8) with MK-677 and a decrease of 0.4 kg (−1.1-0.4) with placebo. Total ASM was also significantly increased from baseline at 6 and 12 months, and vs. placebo (P<0.001).

Figure 4:
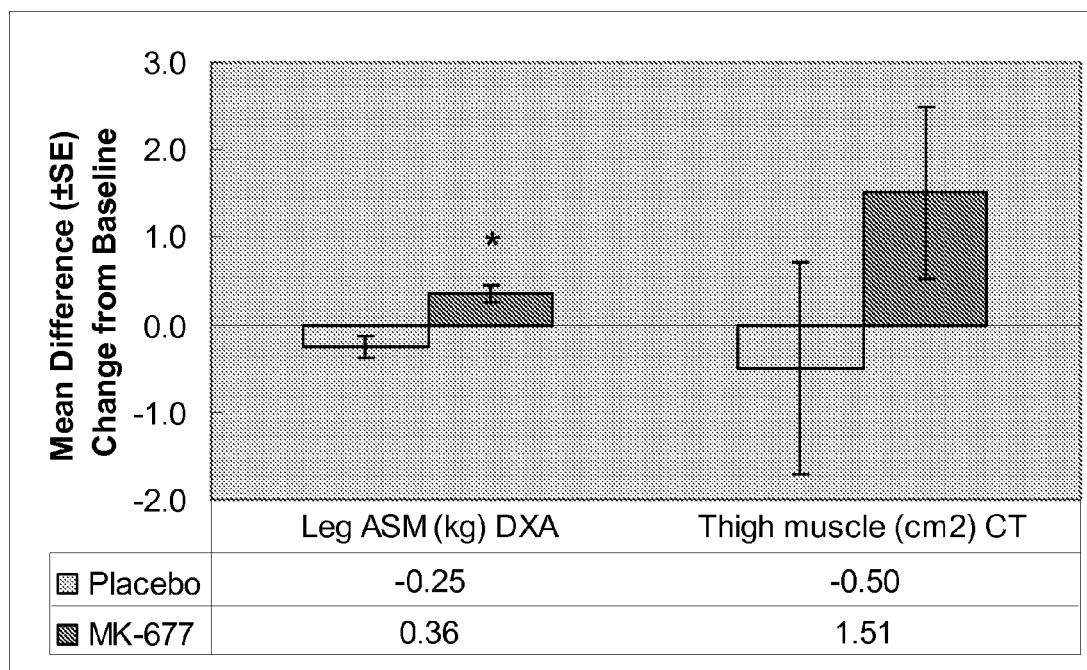
FIG. 4: Change in leg ASM and thigh muscle are shown. With placebo there was a trend vs. baseline (P=0.08) for a decline in leg ASM; however, leg ASM increased significantly vs. baseline with MK-677 treatment (P<0.001) and this was significantly different from placebo at 12 months (P<0.001). However, this was not confirmed when thigh muscle area was measured by CT (P=0.2 vs. placebo). This is probably explained by CT measurement being two dimensional measurements requiring exact positioning of CT scan section on each occasion while DXA measurement of ASM is three dimensional and is therefore more reproducible.

Leg ASM and Thigh Muscle (FIG. 4). With placebo there was a trend vs. baseline (P=0.08) for a decline in leg ASM; however, leg ASM increased significantly vs. baseline with MK-677 treatment (P<0.001) and this was significantly different from placebo at 12 months (P<0.001). However, with MK-677 the small increase in thigh muscle area measured by CT did not reach statistical significance (P=0.2 vs. placebo).

Body Water and Cell Mass (FIG. 3C). There were no significant changes in TBW, ICW or ECW. However, during one year of placebo there was an absolute loss of cell mass (ICW) that is reflected in a loss of total FFM (FIG. 3B), specifically TASM.

T-Score for $TASM/hr^2$. Individual t-scores for $TASM/ht^2$ at baseline and 12 months are shown in FIG. 5. At the end of year 1, the t-score did not change or declined in 17 of 22 subjects on placebo (FIG. 5A); in the MK-677 group (FIG. 5B), 26 of 43 (60%) had an increase and only 7 of 43 had a decrease in t-score (P<0.001 vs. placebo).

Muscle Strength At 12 months there was no change in total work in knee extension or flexion or in shoulder extension between groups. With placebo, shoulder flexion total work was significantly decreased vs. baseline at 6 months (P=0.04) and 12 months (P=0.01). At 12 months there was a trend for prevention of this decline with MK-677 treatment vs. placebo (P=0.07); this reached statistical significance when the main effect (6 and 12 months together) was calculated (P=0.019).

Function and Quality of Life There were no significant changes in any measurements of function or quality of life.

Glucose Metabolism

Insulin resistance estimated by Quicki increased significantly after 6 and 12 months of treatment with MK-677 (P<0.001 vs. placebo), but remained in the normal range for non-obese adults based on the data from Katz et al. (11). Although there were slight elevations in hemoglobin A1c levels in most subjects on MK-677, they remained asymptomatic and these individuals tended to have higher BMI and HBA1c levels and reduced insulin sensitivity at baseline. An 81-year-old man had an increase in HBA1c and fasting blood glucose after crossover from placebo to MK-677 (with a transient elevation in PSA as well); his dose was reduced to 10 mg per day and the HBA1c returned to normal after a low carbohydrate diet was started.

Adverse Effects The most frequently reported side effect was an increase in appetite in 29/43 on MK-677 vs. 8/22 on placebo; appetite returned to normal within 3 months in about one-half the subjects, and more gradually in others. Other notable side effects included mild, transient edema (19/43 vs. 6/22 on placebo) and transient muscle pain (14/43 vs. 2/22 on placebo). Joint pain was reported in both groups (25/43 vs. 17/22 on placebo).

Serious adverse effects occurred in the following individuals on MK-677 treatment. An 82-year-old woman developed an adenocarcinoma of the tongue which was diagnosed at 12 months (data not included, probably not related) and another 68-year-old woman had a myocardial infarction 7 days after starting MK-677 (not related). One man was diagnosed with a renal cell carcinoma, an incidental finding during a study-related CT scan—he had been on placebo for 6 months.

PSA levels remained in the normal range and in fact, declined significantly with MK-677 treatment; an elevated PSA in one 81-year-old man (noted above) returned to normal after back-titration. There were no changes in mammograms or pap smears during the 2 years of the study and there were no changes in routine laboratory tests.

Bibliography for Example 2

(1) Chapman I M, Bach M A, Van Cauter E, Farmer M, Krupa D, Taylor A M et al. Stimulation of the growth hormone (GH)-insulin-like growth factor I axis by daily oral administration of a GH secretagogue (MK-677) in healthy elderly subjects. J Clin Endocrinol Metab 1996; 81:4249-4257.

(2) Chapman I M, Hartman M L, Straume M, Johnson M L, Veldhuis J D, Thorner M O. Enhanced sensitivity growth hormone (GH) chemiluminescence assay reveals lower postglucose nadir GH concentrations in men than women. J Clin Endocrinol Metab 1994; 78:1312-1319.

(3) Johnson M L, Virostko A, Veldhuis J D, Evans W S. Deconvolution analysis as a hormone pulse-detection algorithm. Methods Enzymol 2004; 384:40-54.

(4) Katz A, Nambi S S, Mather K, Baron A D, Follmann D A, Sullivan G et al. Quantitative insulin sensitivity check index: a simple, accurate method for assessing insulin sensitivity in humans. J Clin Endocrinol Metab 2000; 85(7): 2402-2410.

(5) Heymsfield S B, Lichtman S, Baumgartner R N, Wang J, Kamen Y, Aliprantis A et al. Body composition of humans: comparison of two improved four-compartment models that differ in expense, technical complexity, and radiation exposure. Am J Clin Nutr 1990; 52:52-58.

(6) Clasey J L, Kanaley J A, Wideman L, Heymsfield S B, Teates C D, Gutgesell M E et al. Validity of methods of body composition assessment in young and older men and women. J Appl Physiol 1999; 86:1728-1738.

(7) Heymsfield S B, Smith R, Aulet M, Bensen B, Lichtman S, Wang J et al. Appendicular skeletal muscle mass: measurement by dual-photon absorptiometry. Am J Clin Nutr 1990; 52:214-218.

(8) Clasey J L, Bouchard C, Wideman L, Kanaley J, Teates C D, Thorner M O et al. The influence of anatomical boundaries, age and sex on the assessment of abdominal visceral fat. Obesity Res 1997; 5:395-401.

(9) Silva A M, Wang J, Pierson R N, Jr., Wang Z, Heymsfield S B, Sardinha L B et al. Extracellular water: greater expansion with age in African Americans. J Appl Physiol 2005; 99:261-267.

(10) Schoeller D A, van Santen E, Peterson D W, Dietz W, Jaspan J, Klein P D. Hydrometry. In: Roche A F, Heymsfield S B, Lohman T G, editors. Human Body Composition. Champagne, Ill.: Human Kinetics, 1996: 25-49.

(11) Plotkin D, Ng J, Farmer M, Gelato M, Kaiser F, Kiel D et al. Use of MK-677, an oral GH secretagogue in frail elderly subjects. Endocrinology and Metabolism, Proceedings of GH Research Society Conference, London 4(Suppl.A), 35-36. 1997.

(12) Gallagher D, Visser M, De Meersman R E, Sepulveda D, Baumgartner R N, Pierson R N et al. Appendicular skeletal muscle mass: effects of age, gender, and ethnicity. J Appl Physiol 1997; 83:229-239.

(13) Baumgartner R N, Koehler K M, Gallagher D, Romero L, Heymsfield S B, Ross R R et al. Epidemiology of sarcopenia among the elderly in New Mexico. Am J Epidemiol 1998; 147:755-763.

(14) Baumgartner R N, Koehler K M, Gallagher D, Romero L, Heymsfield S B, Ross R R et al. RE: "Epidemiology of sarcopenia among the elderly in New Mexico". Am J Epidemiol 1999; 149:1160.

(15) Murphy M G, Weiss S, McClung M, Schnitzer T, Cerchio K, Connor J et al. Effect of alendronate and MK-677 (a growth hormone secretagogue), individually and in combination, on markers of bone turnover and bone mineral density in postmenopausal osteoporotic women. J Clin Endocrinol Metab 2001; 86:1116-1125.

(16) Tabachnick B G, Fidell L S. Using multivariate statistics. 5th ed. Pearson Education, Inc., 2007.

The invention should not be construed to be limited solely to the assays and methods described herein, but should be construed to include other methods and assays as well. Other methods which were used but not described herein are well known and within the competence of one of ordinary skill in the art of chemistry, biochemistry, molecular biology, and clinical medicine. One of ordinary skill in the art will know that other assays and methods are available to perform the procedures described herein.

The abbreviations used herein have their conventional meaning within the clinical, chemical, and biological arts. In the case of any inconsistencies, the present disclosure, including any definitions therein will prevail.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. Accordingly, the present invention is not intended to be limited to the embodiments shown herein but is to be accorded the widest scope consistent with the principles and novel features disclosed herein.

What is claimed is:

1. A method of maintaining or increasing muscle mass to treat sarcopenia, comprising: administering to a patient in need thereof a therapeutically effective amount of a growth hormone secretagogue.

2. The method of claim 1, wherein the patient has a t-score selected from (a)$\leq-3$, (b)$\leq-2.5$ (c), $\leq-2$, (d)$\leq-1.5$, (e)$\leq-1.0$, and (f)$\leq-0.5$.

3. The method of claim 1, wherein the age of the patient is selected from at least (a) 40, (b) 50, (c) 55, (d) 60, (e) 65, and (f) 70.

4. The method of claim 1, wherein the age range of the patient is selected from (a) 40-50, (b) 50-60, and (c) 60-70.

5. The method of claim 1, wherein the patient's t-score is increased after at least one year of treatment.

6. The method of claim 1, wherein the patient's t-score is unchanged after at least one year of treatment.

7. The method of claim 1, wherein the patient has suffered some loss of muscle mass, but does not suffer from a condition that interferes with acts of daily living and/or prevents the subject from living an independent life.

8. The method of claim 1, wherein the patient is considered vulnerable to developing sarcopenia.

9. The method of claim 8, wherein the patient falls into at least one of the following categories (a) uses glucocorticoid steroids, (b) has a chronic infection, (c) has a chronic inflammatory condition, and (d) has cancer.

10. A method of maintaining or increasing muscle mass to treat sarcopenia, comprising: administering to a patient in need thereof a therapeutically effective amount of a pharmaceutical composition, comprising: a growth hormone secretagogue and a pharmaceutically acceptable carrier.

11. The method of claim 1, wherein the growth hormone secretagogue is selected from
1) N-[1(R)-[(1,2-Dihydro-1-methanesulfonylspiro[3H-indole-3,4'-piperidin]-1'-yl)carbonyl]-2-(1H-indol-3-yl)ethyl]-2-amino-2-methylpropanamide;
2) N-[1(R)-[(1,2-Dihydro-1-methanecarbonylspiro[3H-indole-3,4'-piperidin]-1'-yl)carbonyl]-2-(1H-indol-3-yl)ethyl]-2-amino-2-methylpropanamide;
3) N-[1(R)-[(1,2-Dihydro-1-benzenesulfonylspiro[3H-indole-3,4'-piperidin]-1'-yl)carbonyl]-2-(1H-indol-3-yl)ethyl]-2-amino-2-methylpropanamide;

4) N-[1(R)-[(3,4-Dihydro-spiro[2H-1-benzopyran-2,4'-piperidin]-1'-yl)carbonyl]-2-(1H-indol-3-yl)ethyl]-2-amino-2-methylpropanamide;

5) N-[1(R)-[(2-Acetyl-1,2,3,4-tetrahydrospiro[isoquinolin-4,4'-piperidin]-1'-yl)carbonyl]-2-(indol-3-yl)ethyl]-2-amino-2-methyl-propanamide;

6) N-[1(R)-[(1,2-Dihydro-1-methanesulfonylspiro[3H-indole-3,4'-piperidin]-1'-yl)carbonyl]-2-(phenylmethyloxy)ethyl]-2-amino-2-methylpropanamide;

7) N-[1(R)-[(1,2-Dihydro-1-methanesulfonylspiro[3H-indole-3,4'-piperidin]-1'-yl)carbonyl]-2-(phenylmethyloxy)ethyl]-2-amino-2-methylpropanamide mesylate salt;

8) N-[1(R)-[(1,2-Dihydro-1-methanesulfonylspiro[3H-indole-3,4'-piperidin]-1'-yl)carbonyl]-2-(2',6'-difluorophenylmethyloxy)ethyl]-2-amino-2-methylpropanamide;

9) N-[1(R)-[(1,2-Dihydro-1-methanesulfonyl-5-fluorospiro[3H-indole-3,4'-piperidin]-1'-yl)carbonyl]-2-(phenylmethyloxy)ethyl]-2-amino-2-methylpropanamide;

10) N-[1(S)-[(1,2-Dihydro-1-methanesulfonylspiro[3H-indole-3,4'-piperidin]-1'-yl) carbonyl]-2-(phenylmethylthio)ethyl]-2-amino-2-methylpropanamide;

11) N-[1(R)-[(1,2-Dihydro-1-methanesulfonylspiro[3H-indole-3,4'-piperidin]-1'-yl)carbonyl]-3-phenylpropyl]-2-amino-2-methylpropanamide;

12) N-[1(R)-[(1,2-Dihydro-1-methanesulfonylspiro[3H-indole-3,4'-piperidin]-1'-yl)carbonyl]-3-cyclohexylpropyl]-2-amino-2-methylpropanamide;

13) N-[1(R)-[(1,2-Dihydro-1-methanesulfonylspiro[3H-indole-3,4'-piperidin]-1'-yl)carbonyl]-4-phenylbutyl]-2-amino-2-methylpropanamide;

14) N-[1(R)-[(1,2-Dihydro-1-methanesulfonylspiro[3H-indole-3,4'-piperidin]-1'-yl)carbonyl]-2-(5-fluoro-1H-indol-3-yl)ethyl]-2-amino-2-methylpropanamide;

15) N-[1(R)-[(1,2-Dihydro-1-methanesulfonyl-5-fluorospiro[3H-indole-3,4'-piperidin]-1'-yl)carbony]-2-(5-fluoro-1H-indol-3-yl)ethyl]-2-amino-2-methylpropanamide;

16) N-[1(R)-[(1,2-Dihydro-1-(2-ethoxycarbonyl)methylsulfonylspiro-[3H-indole-3,4'-piperidin]-1'-yl)carbonyl]-1-(1H-indol-3-yl)ethyl]-2-amino-2-methylpropanamide;

17) N-[1(R)-[(1,2-Dihydro-1,1-dioxospiro[3H-benzothiophene-3,4'-piperidin]-1'-yl)carbonyl]-2-(phenylmethyloxy)ethyl]-2-amino-2-methylpropanamide;

and pharmaceutically acceptable salts thereof.

12. The method of claim 1, wherein the growth hormone secretagogue is (N-[1(R)-[(1,2-dihydro-1-methanesulfonylspiro[3H-indole-3,4'-piperidin]-1'-yl)carbonyl]-2-(phenylmethyloxy)ethyl]-2-amino-2-methylpropanamide methanesulfonate (ibutamoren mesylate)).

13. The method of claim 10, wherein the growth hormone secretagogue is selected from 1) N-[1(R)-[(1,2-Dihydro-1-methanesulfonylspiro[3H-indole-3,4'-piperidin]-1'-yl)carbonyl]-2-(1H-indol-3-yl)ethyl]-2-amino-2-methylpropanamide;

2) N-[1(R)-[(1,2-Dihydro-1-methanecarbonylspiro[3H-indole-3,4'-piperidin]-1'-yl)carbonyl]-2-(1H-indol-3-yl)ethyl]-2-amino-2-methylpropanamide;

3) N-[1(R)-[(1,2-Dihydro-1-benzenesulfonylspiro[3H-indole-3,4'-piperidin]-1'-yl)carbonyl]-2-(1H-indol-3-yl) ethyl]-2-amino-2-methylpropanamide;

4) N-[1(R)-[(3,4-Dihydro-spiro[2H-1-benzopyran-2,4'-piperidin]-1'-yl)carbonyl]-2-(1H-indol-3-yl)ethyl]-2-amino-2-methylpropanamide;

5) N-[1(R)-[(2-Acetyl-1,2,3,4-tetrahydrospiro[isoquinolin-4,4'-piperidin]-1'-yl)carbonyl]-2-(indol-3-yl)ethyl]-2-amino-2-methyl-propanamide;

6) N-[1(R)-[(1,2-Dihydro-1-methanesulfonylspiro[3H-indole-3,4'-piperidin]-1'-yl)carbonyl]-2-(phenylmethyloxy)ethyl]-2-amino-2-methylpropanamide;

7) N-[1(R)-[(1,2-Dihydro-1-methanesulfonylspiro[3H-indole-3,4'-piperidin]-1'-yl)carbonyl]-2-(phenylmethyloxy)ethyl]-2-amino-2-methylpropanamide mesylate salt;

8) N-[1(R)-[(1,2-Dihydro-1-methanesulfonylspiro[3H-indole-3,4'-piperidin]-1'-yl)carbonyl]-2-(2',6'-difluorophenylmethyloxy)ethyl]-2-amino-2-methylpropanamide;

9) N-[1(R)-[(1,2-Dihydro-1-methanesulfonyl-5-fluorospiro[3H-indole-3,4'-piperidin]-1'-yl)carbonyl]-2-(phenylmethyloxy)ethyl]-2-amino-2-methylpropanamide;

10) N-[1(S)-[(1,2-Dihydro-1-methanesulfonylspiro[3H-indole-3,4'-piperidin]-1'-yl) carbonyl]-2-(phenylmethylthio)ethyl]-2-amino-2-methylpropanamide;

11) N-[1(R)-[(1,2-Dihydro-1-methanesulfonylspiro[3H-indole-3,4'-piperidin]-1'-yl)carbonyl]-3-phenylpropyl]-2-amino-2-methylpropanamide;

12) N-[1(R)-[(1,2-Dihydro-1-methanesulfonylspiro[3H-indole-3,4'-piperidin]-1'-yl)carbonyl]-3-cyclohexylpropyl]-2-amino-2-methylpropanamide;

13) N-[1(R)-[(1,2-Dihydro-1-methanesulfonylspiro[3H-indole-3,4'-piperidin]-1'-yl)carbonyl]-4-phenylbutyl]-2-amino-2-methylpropanamide;

14) N-[1(R)-[(1,2-Dihydro-1-methanesulfonylspiro[3H-indole-3,4'-piperidin]-1'-yl)carbonyl]-2-(5-fluoro-1H-indol-3-yl)ethyl]-2-amino-2-methylpropanamide;

15) N-[1(R)-[(1,2-Dihydro-1-methanesulfonyl-5-fluorospiro[3H-indole-3,4'-piper idin]-1'-yl)carbony]-2-(5-fluoro-1H-indol-3-yl)ethyl]-2-amino-2-methylpropanamide;

16) N-[1(R)-[(1,2-Dihydro-1-(2-ethoxycarbonyl)methylsulfonylspiro-[3H-indole-3,4'-piperidin]-1'-yl)carbonyl]-1-(1H-indol-3-yl)ethyl]-2-amino-2-methylpropanamide;

17) N-[1(R)-[(1,2-Dihydro-1,1-dioxospiro[3H-benzothiophene-3,4'-piperidin]-1'-yl)carbonyl]-2-(phenylmethyloxy)ethyl]-2-amino-2-methylpropanamide;

and pharmaceutically acceptable salts thereof.

14. The method of claim 10, wherein the growth hormone secretagogue is (N-[1(R)-[(1,2-dihydro-1-methanesulfonylspiro[3H-indole-3,4'-piperidin]-1'-yl)carbonyl]-2-(phenylmethyloxy)ethyl]-2-amino-2-methylpropanamide methanesulfonate (ibutamoren mesylate)).

* * * * *